(12) United States Patent
Mori et al.

(10) Patent No.: US 7,381,195 B2
(45) Date of Patent: Jun. 3, 2008

(54) HEMATOCRIT SENSOR

(75) Inventors: Yoshihiro Mori, Shizuoka (JP); Takayuki Ohishi, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 395 days.

(21) Appl. No.: 10/623,178

(22) Filed: Jul. 18, 2003

(65) Prior Publication Data
US 2004/0067594 A1    Apr. 8, 2004

(30) Foreign Application Priority Data

| Jul. 18, 2002 | (JP) | 2002-209330 |
| May 13, 2003 | (JP) | 2003-134906 |

(51) Int. Cl.
*A61M 37/00* (2006.01)
*C02F 1/44* (2006.01)
*G01N 33/48* (2006.01)

(52) U.S. Cl. ............... 604/6.08; 604/4.01; 604/6.09; 210/745; 356/39

(58) Field of Classification Search ......... 604/4.01, 604/5.01, 5.04, 6.01, 6.08, 6.09, 6.11, 65–67; 210/645, 646, 739, 745, 195.2, 416.1, 433.1; 422/44, 48; 600/322; 436/70; 137/93; 356/39, 356/336; 73/36

See application file for complete search history.

(56) References Cited

U.S. PATENT DOCUMENTS

| 4,082,461 A | * | 4/1978 | Mould | ............... 356/332 |
| 4,745,279 A | * | 5/1988 | Karkar et al. | ............... 250/343 |
| 5,291,884 A | * | 3/1994 | Heinemann et al. | ........ 600/322 |
| 5,385,539 A | * | 1/1995 | Maynard | .................. 604/6.08 |
| 5,838,429 A | * | 11/1998 | Hahn | ........................ 356/39 |
| 6,554,788 B1 | * | 4/2003 | Hunley et al. | ............. 604/4.01 |
| 6,582,385 B2 | * | 6/2003 | Burbank et al. | ........... 604/5.04 |
| 6,660,995 B1 | * | 12/2003 | Canpolat et al. | ....... 250/227.23 |

FOREIGN PATENT DOCUMENTS

| JP | 62251662 | 11/1987 |
| JP | 11 221275 | 8/1999 |
| JP | 11 226119 A | 8/1999 |
| JP | 2001-540 | 1/2001 |

* cited by examiner

*Primary Examiner*—Leslie R Deak
(74) *Attorney, Agent, or Firm*—Darby & Darby P.C.

(57) ABSTRACT

The present invention relates to a hematocrit sensor and a method for measuring hematocrit values using such a device, which comprises a hematocrit sensor in a blood circuit that measures hematocrit value, a blood purifier that purifies a patient's blood while extracorporeally circulating the patient's blood, a housing having a slot connected to a portion of the blood circuit, a slit or plurality of pores built in the slot of the housing, and a light emission means and a light reception means positioned in the housing such that both means face the blood circuit through the slit or the plurality of pores.

19 Claims, 14 Drawing Sheets

Effect of Slit Width

HEMATOCRIT SENSOR

BACKGROUND OF THE INVENTION

The present invention relates to a hematocrit sensor and a method for measuring hematocrit concentration which, indicates the blood concentration in a blood circuit of a blood purifier that circulates and purifies the blood of a patient.

In dialysis treatments, a blood circuit consisting mainly of flexible tubing is used to place the blood of a patient in extracorporeal blood circulation. This blood circuit arrangement includes an arterial blood circuit having an arterial needle at one end to collect the blood from the patient and a venous blood circuit having a venous needle at one end to return the blood to the patient. A dialyzer can be incorporated between the arterial blood circuit and the venous blood circuit.

A roller blood pump is placed in the arterial blood circuit. By driving the pump, the blood of the patient is collected through the arterial needle and flows extracorporeally through the arterial blood circuit, the dialyzer, and the venous blood circuit. There are multiple hollow fibers inside the dialyzer. The blood flows through each hollow fiber.

Two projections are formed on the dialyzer case, one being a dialyzing fluid inlet port and the other being a dialyzing fluid outlet port. A dialysis device is connected to the two ports. The dialysis device supplies dialyzing fluid of predetermined concentration in through the dialyzing fluid inlet port, along the outside of the hollow fibers (i.e., between the outside surface of the hollow fibers and the inside surface of the dialyzer case), and then out through the dialyzing fluid outlet port.

The walls of hollow fibers, which contain micropores, form blood purifying membranes. Waste products of the blood passing through the inside of the hollow fibers are dialyzed to the dialyzing fluid through the blood purifying membrane and the purified blood returns to the patient. To remove water from the blood of the patient during the dialysis treatment, the dialysis monitor can include an ultrafiltration pump.

The amount of water to be removed (water removal rate) is regulated by controlling the driving speed of the ultrafiltration pump. However, if too much water is removed or if water is removed too quickly, the volume of the circulating blood of the patient is excessively reduced such that blood pressure drop or shock may be induced. On the other hand, if the water removal rate is too low, the treatment duration may be prolonged and the burden to the patient can be too great.

Therefore, as disclosed in Japanese laid open patent publication number Hei 11-221275 and Japanese laid open patent publication number 2001-540, there are blood treatment devices that control the rate of water removal while monitoring the condition of the patient. These existing blood treatment devices have used hematocrit values and other blood parameters to monitor the condition of a patient's blood. The hematocrit value is an indicator of blood concentration, and is expressed as the ratio of red blood cell volume to whole blood volume.

In general, although the hematocrit value during water removal may be in the range of 10 to 60%, the actual value during water removal would be higher than the normal value if the patient experiences shock or blood pressure drop as a result of excess water removal volume or excess water removal rate. By monitoring hematocrit values in real time during water removal that occurs as part of dialysis treatment, the real time measured values could be used as a basis for controlling the driving of the ultrafiltration pump. Based on this parameter, an appropriate water removal rate could be set, which exerts the least burden on the patient. A means for monitoring hematocrit values and controlling the ultrafiltration pump can comprise a blood circuit (for example, a flexible tube) that is arranged between a light emission means and a light reception means. The light emission means and light reception means face each other. The light emission means emits irradiated light, which is received by the light reception means. Accordingly, the rate of light transmitted through the blood in the blood circuit can be measured, and the hematocrit value can be obtained based on this measurement.

OBJECTS OF THE INVENTION

Existing light transmission type hematocrit sensors generally position the blood circuit between the light emission means and the light reception means. In this manner, the blood circuit must be sandwiched between the light emission means and the light reception means, which can cause the blood circuit to be deformed. Specifically, the blood circuit in a transmission type sensor must be tightly held to increase the accuracy of the measurement. Thus, the force used to hold the blood circuit in place will deform the flexible tube of the blood circuit. Consequently, blood flow rate decreases, and the load on the blood circuit increases.

Additionally, a housing for the light emission means must be built independently of a housing for the light reception means. The two housinges must then be combined to provide one sensor. Accordingly, the total size of the sensor will be larger and more difficult to handle.

The object of the present invention is to overcome the problems of the aforementioned hematocrit sensors and to provide a hematocrit sensor that can more accurately measure hematocrit values while avoiding deformation of the flexible tube of the blood circuit, and allowing for the total size of the sensor to be reduced.

Figure 1:
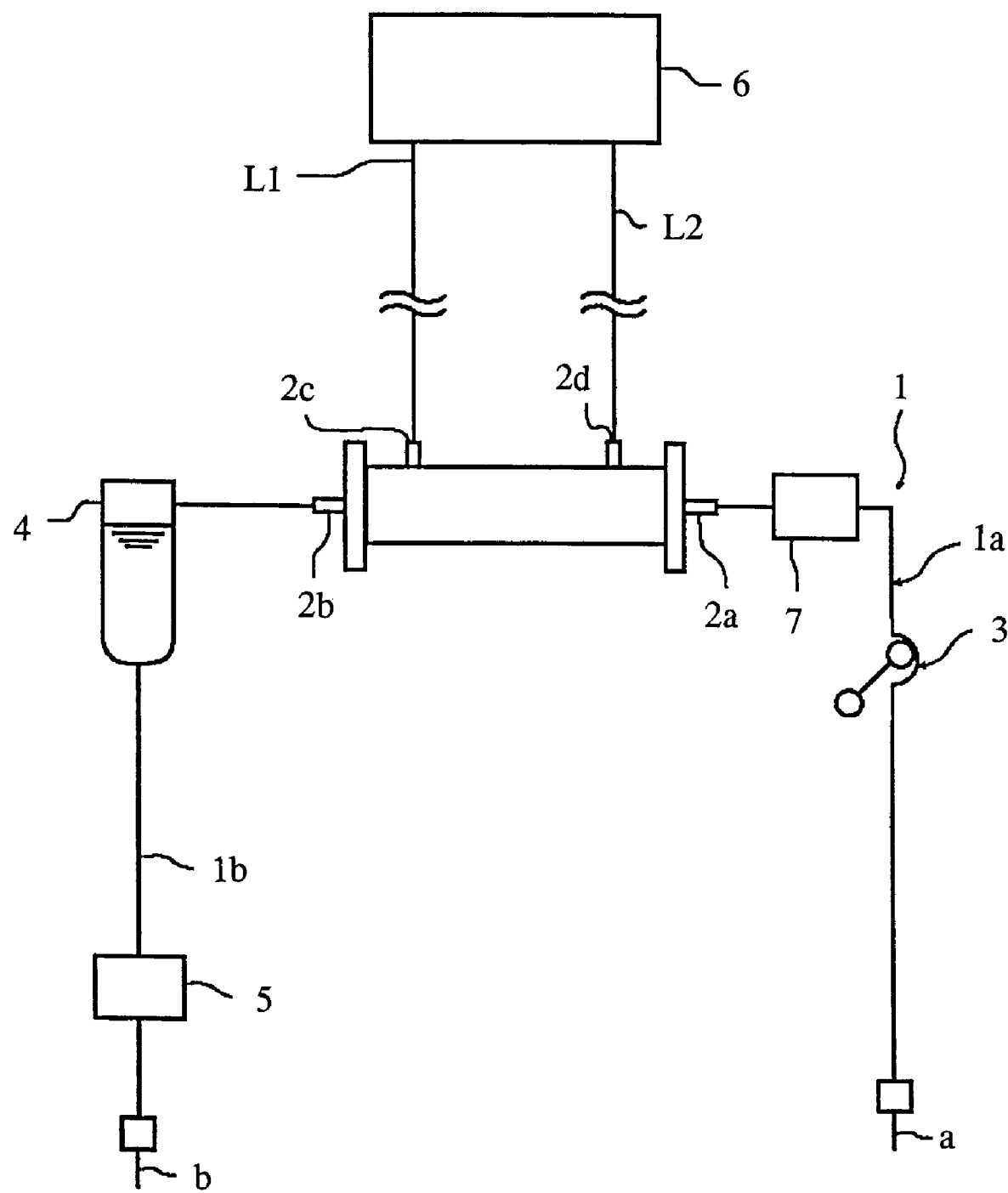
FIG. 1 is a schematic drawing of a blood circuit and a dialysis monitor comprising a hematocrit sensor of the present invention.

LIST OF REFERENCE NUMERALS 1 blood circuit; 1a arterial blood circuit; 1b venous blood circuit; 2 dialyzer; 2a blood inlet port; 2b blood outlet port; 2c dialyzing fluid inlet port; 2d dialyzing fluid outlet port; 3 blood pump; 4 drip chamber; 5 air bubble detector; 6 dialysis monitor; 7 hematocrit sensor; 8 ultrafiltration pump; 9 heater; 10 deaeration means; 11/11' housing; 11a slot; 11b concave part; 11c convex part; 11d convex part; 12/12' slit; 13 light emission means; 14 light reception means; 15/15' cover; 16 hook; 16a top part; 17 pin; 18 swing pin; 19 pin; 20 base board; 21 plate; 22 holder; 23 fixing means; 23a lobe; 24a board; 24b board; 24aa long hole; 24ba long hole; 25 detecting means; 25a push button portion; 26 cover; a arterial needle; b venous needle; C flexible tube; L1 dialyzing fluid inlet line; L2 dialyzing fluid outlet line; L3 bypass line; n1 screw; n2 screw; N fixed screw; P duplex pump; S space; ST stand; w1 washer; w2 washer.

SUMMARY OF THE INVENTION

The present invention comprises a hematocrit sensor positioned in a blood circuit of a dialyzer that extracorporeally circulates and purifies the blood of a patient. The hematocrit sensor measures the hematocrit value, which is indicative of blood concentration. The hematocrit sensor further comprises a housing having a slot to contain a part of the blood circuit. The slot of the housing comprises a slit or a plurality of pores. The housing comprises a light emission means and a light reception means such that both means face the blood circuit through the aforementioned slit or plurality of pores. The light emission means emits irradiated light to the blood flowing through the blood circuit, and the light reception means receives the light reflected from the blood.

Another embodiment of the invention comprises a means for measuring hematocrit value by the hematocrit sensor described above, wherein the housing includes a means for covering the slot comprising the slit or plurality of pores.

Another embodiment of the invention comprises a hematocrit sensor as described in the above embodiment, wherein the cover is built so as to be freely movable on the housing, such that the slot can be opened and closed.

Yet another embodiment of the invention comprises a hematocrit sensor as described in any of the above embodiments further comprising a holding means to keep the cover securely in place.

Another embodiment of the invention comprises a hematocrit sensor as described in any of the above embodiments, wherein the slot comprises a detection means for detecting when the blood circuit is contained in the slot and the cover is closed.

Another embodiment of the invention comprises a hematocrit sensor as described in any of the above embodiments, wherein the blood circuit comprises a dialyzer connected in the middle of the blood circuit, in which the patient's blood is extracorporeally circulated for dialysis treatment, and based on the measured hematocrit value, controls the ultrafiltration pump in order to remove water, controls a substitution fluid condition, or controls a dialyzing fluid condition.

Yet another embodiment of the invention comprises a hematocrit sensor as described in any of the above embodiments, wherein the blood circuit comprises a drip chamber connected to the blood circuit, and a means for fixing the drip chamber is integrally formed with a means for fixing the housing.

Another embodiment of the invention comprises a hematocrit sensor as described in any of the above embodiments, wherein the blood circuit comprises an air bubble detector connected to the blood circuit.

Another embodiment of the invention comprises a hematocrit sensor as described in any of the above embodiments, wherein the blood circuit comprises a blood detector connected to the blood circuit to detect the presence of blood. Hematocrit value measurement begins when blood is detected by the blood detector. This initial measurement acts as a benchmark.

Yet another embodiment of the invention comprises a hematocrit sensor as described in any of the above embodiments, wherein the width of the slit or the diameter of the pores can be arbitrarily adjusted.

Another embodiment of the invention comprises a hematocrit sensor as described in any of the above embodiments, wherein the measured hematocrit value can be compensated based on the reflected light received by the light reception means when the light is off while the light emission means is flashing.

Another embodiment of the invention comprises a hematocrit sensor as described in any of the above embodiments, wherein the measured hematocrit value can be compensated in accordance with the blood flow rate in the blood circuit.

DETAILED DESCRIPTION OF THE INVENTION

According to one embodiment of the present invention, the hematocrit sensor is of the so-called reflection type. Accordingly, deformation of the flexible tube of the blood circuit can be avoided, and the overall size of the hematocrit sensor can be reduced. Further, the light irradiated from the light emission means and the reflected light returning to the light reception means pass through the slit or plurality of pores, allowing for more accurate measurement to be performed.

According to another embodiment of the invention, the housing includes a cover, such that the slot, including the slit or plurality of pores, can be covered while measurement is being performed. Thus, the effects of ambient light can be avoided, and a more accurate measurement of hematocrit value can be made.

According to another embodiment of the invention, the housing includes a cover that can swing freely, such that the slot, including the slit or plurality of pores, can be either opened or closed. Thus, the cover can be closed during measurement, while it is a part of the blood circuit. Alternatively, at times other than during measurement, the cover can be swung open and the hematocrit sensor can be removed from the blood circuit. Consequently, operational productivity can be increased when the sensor is fixed on the blood circuit or when it is removed from the blood circuit.

According to yet another embodiment of the invention, the housing includes a holding means which can prevent the cover from moving while the cover is covering the slot, including the slit or plurality of pores, such that the sensor is prevented from sliding out of position after being set, or if the cover is carelessly opened. Thus, the hematocrit value can be more accurately measured.

According to another embodiment of the invention, the detection means for detecting whether or not the cover is closed, can also detect whether or not the blood circuit is contained in the slot. Thus, instances of forgetting to set the blood circuit to the hematocrit sensor and to close the cover can be avoided.

According to another embodiment of the invention, the hematocrit sensor is placed in a blood circuit for dialysis treatment, in which a patient's blood is extracorporeally circulated. The hematocrit sensor can control the water removal rate, substitution fluid condition, and dialyzing fluid condition based on the measured hematocrit values, such that medical treatment suitable to the patient can be performed.

According to yet another embodiment of the invention, the hematocrit sensor and the means for fixing the drip chamber are integrally formed, such that the hematocrit system can be simplified and reduced in overall size. In contrast, the hematocrit system would be more complex and larger in size if the components were built and arranged separately.

According to another embodiment of the invention, the hematocrit sensor and the air bubble detector are integrally formed, such that the hematocrit system can be simplified and reduced in overall size. In contrast, the hematocrit system would be more complex and larger in size if the components were built and arranged separately.

According to another embodiment of the invention, the hematocrit sensor and the blood detector are integrally formed, such that the hematocrit value measurement starts at the point when the blood detector detects the blood flow. Thus, hematocrit values at every measurement can be accurately compared, and the hematocrit value measurement can be more accurately performed.

According to yet another embodiment of the invention, the width of the slit or the diameter of the plurality of pores is arbitrarily adjustable. The slit width or pore diameter can be adjusted in accordance with the proportional relationship between the hematocrit value and the measurement value at the light reception means. Therefore, the hematocrit value can be more accurately measured. Further, the effect of differences among the flexible tubes can be considered, avoiding measurement error against the hematocrit value.

According to another embodiment of the invention, the measured value is compensated based on the amount of light reflected to the light reception means when the light is turned off while the light emission means is flashing. Thus, the measurement error due to the ambient light can be avoided, the accuracy of the measurement can be increased, and the safety of the medical equipment can be increased. Furthermore, the composition of the seal protecting the slit from the ambient light can be simplified and eliminated, thereby simplifying the arrangement of the hematocrit sensor itself.

According to another embodiment of the invention, the measured hematocrit value is compensated based on the blood flow rate through the blood circuit, such that the error due to the blood flow rate can be avoided and a more accurate measurement of the hematocrit value can be obtained.

In the following embodiments, the invention will be specifically described in accordance with the figures.

According to the embodiment shown in FIG. 1, a hematocrit sensor is placed in the blood circuit 1 and measures the hematocrit value, which indicates the concentration of the patient's blood flowing through the blood circuit 1. The blood circuit 1 mainly comprises an arterial blood circuit 1a and a venous blood circuit 1b. A dialyzer 2 is connected between the arterial blood circuit 1a and the venous blood circuit 1b.

An arterial needle a is connected at the terminal of the arterial blood circuit 1a and a roller blood pump 3 is positioned at some point in the middle of the arterial blood circuit 1a. Additionally, a venous needle b is connected at the terminal of the venous blood circuit 1b and a drip chamber 4 is connected at some point in the middle of the venous blood circuit 1b.

When the blood pump 3 is driven while the arterial needle a and the venous needle b are inserted into the patient, the patient's blood flows through the arterial blood circuit 1a and into the dialyzer 2. The dialyzer 2 purifies the blood and returns it to the patient through the venous blood circuit 1b after air bubbles are removed by the drip chamber 4. Thus, the blood of the patient is purified by the dialyzer 2 while extracorporeally circulating through the blood circuit 1.

Further, an air bubble detector 5 is placed near the venous needle b in the venous blood circuit 1b. The air bubble detector 5 monitors the presence of air in the blood flowing through the venous blood circuit 1b and can, for example, be formed from a sensor that detects air by applying ultrasound waves to the flexible tubing. Further, the housing for the air bubble detector comprises a blood detector to detect the presence of blood using light irradiation (blood detector not shown). The blood detector can be either a transmission type or a reflection type.

The dialyzer case comprises a blood inlet port 2a, a blood outlet port 2b, a dialyzing fluid inlet port 2c, and a dialyzing fluid outlet port 2d. The blood inlet port 2a and the blood outlet port 2b are connected to the arterial blood circuit 1a and the venous blood circuit 1b, respectively. The dialyzing fluid inlet port 2c and the dialyzing fluid outlet port 2d are connected to a dialyzing fluid inlet line L1 and a dialyzing fluid outlet line L2, respectively. Lines L1 and L2 extend from a dialysis monitor 6.

The dialyzer 2 comprises multiple hollow fibers. The blood flows inside of the hollow fibers and the dialyzing fluid flows between the outside surface of the hollow fibers and the inside surface of the dialyzer case. The hollow fibers include many tiny pores that penetrate the outside and inside surfaces of the hollow fiber membrane, and through which waste products in the blood are dialyzed out to the dialyzing fluid.

Figure 2:
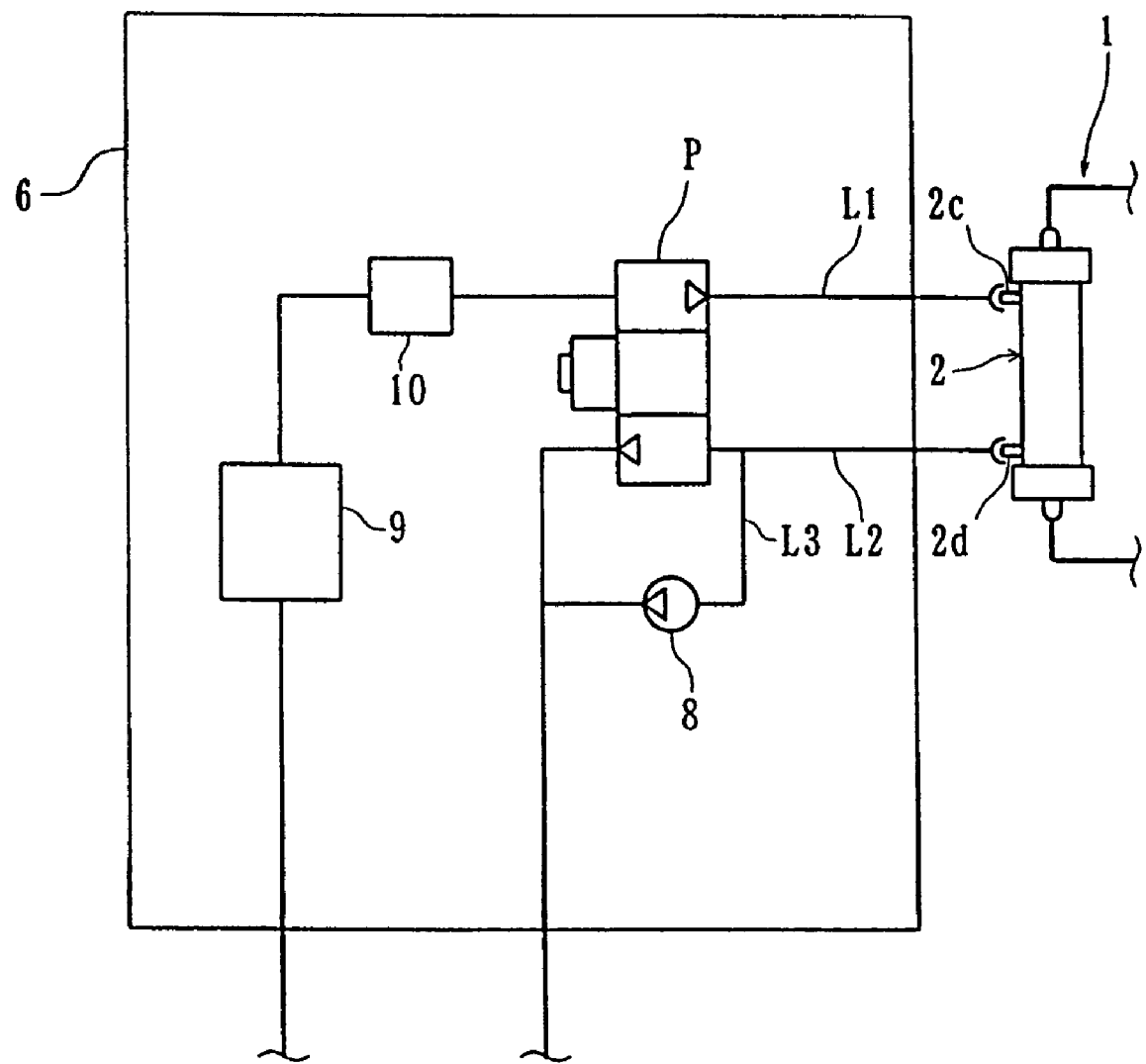
FIG. 2 is a schematic drawing of the dialysis monitor connected to the blood circuit comprising a hematocrit sensor of the present invention.

As shown in FIG. 2, the dialysis monitor 6 comprises a duplex pump P that is connected between the dialyzing fluid inlet line L1 and the dialyzing fluid outlet line L2. A bypass line L3 is connected to the dialyzing fluid outlet line L2, and bypasses the duplex pump P. An ultrafiltration pump 8 is connected to the bypass line L3. Additionally, a first end of the dialyzing fluid inlet line L1 is connected to the dialyzer 2 at the dialyzing fluid inlet port 2c. A second end of the dialyzing fluid inlet line L1 is connected to a dialyzing fluid supplier (not shown), which prepares the dialyzing fluid of predetermined concentration.

A first end of dialyzing fluid outlet line L2 is connected to the dialyzer 2 at the dialyzing fluid outlet port 2d. A second end of dialyzing fluid outlet line L2 is connected to a waste fluid disposal means (not shown).

The dialyzing fluid supplied from the dialyzing fluid supplier passes through the dialyzing fluid inlet line L1 to the dialyzer 2, the passes through the dialyzing fluid outlet line L2 and the bypass line L3, and is let out to the waste fluid disposal means. In FIG. 2, reference numerals 9 and 10 indicate a heater and a deaeration means, both connected to the dialyzing fluid inlet line L1.

The ultrafiltration pump 8 removes water from the patient's blood flowing through the dialyzer 2. When the ultrafiltration pump is activated, the volume of dialyzing fluid let out of the dialyzing fluid outlet line L2 is greater than the volume of the dialyzing fluid introduced from the dialyzing fluid inlet line L1. Accordingly, water is removed from the patient's blood by the difference between the outlet and inlet volumes.

Figure 3A:
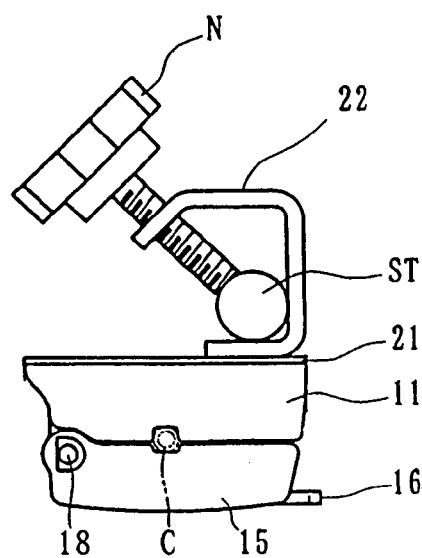
FIG. 3a is a front view of a hematocrit sensor of the present invention.
Figure 3B:
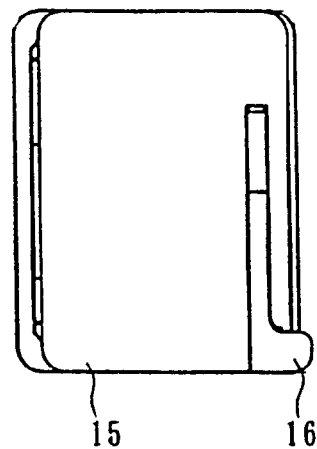
FIG. 3b is a top view of a hematocrit sensor of the present invention.
Figure 3C:
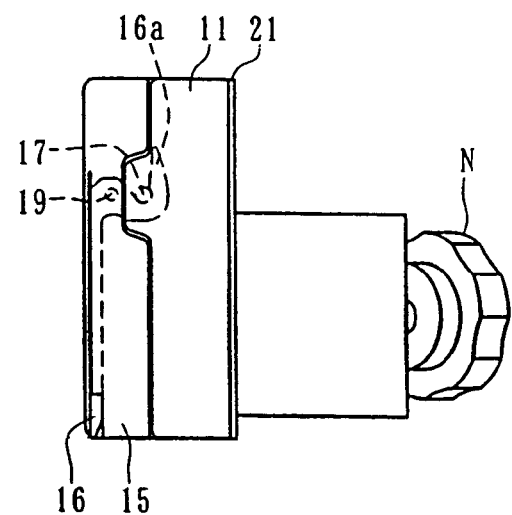
FIG. 3c is a left side view of a hematocrit sensor of the present invention.

According to the above embodiment, the hematocrit sensor 7 is located in the middle of the arterial blood circuit 1a and monitors the patient's blood condition during water removal. The hematocrit sensor 7 as shown in FIGS. 3 to 5 comprises a housing 11, a slit 12, a light emission means 13 (light emission element), a light reception means 14 (light reception element), a cover 15, and a hook 16 as a holding means.

The housing 11 is a resin formed product and comprises the main component of the hematocrit sensor. The slot 11a is formed in the longitudinal direction of the surface of the housing 11. The slot 11a contains part of the flexible tube C in the blood circuit and is molded with the housing 11 when it is built. In addition, the slot 11a preferably has a linear structure having approximately the same width throughout.

Figure 4:
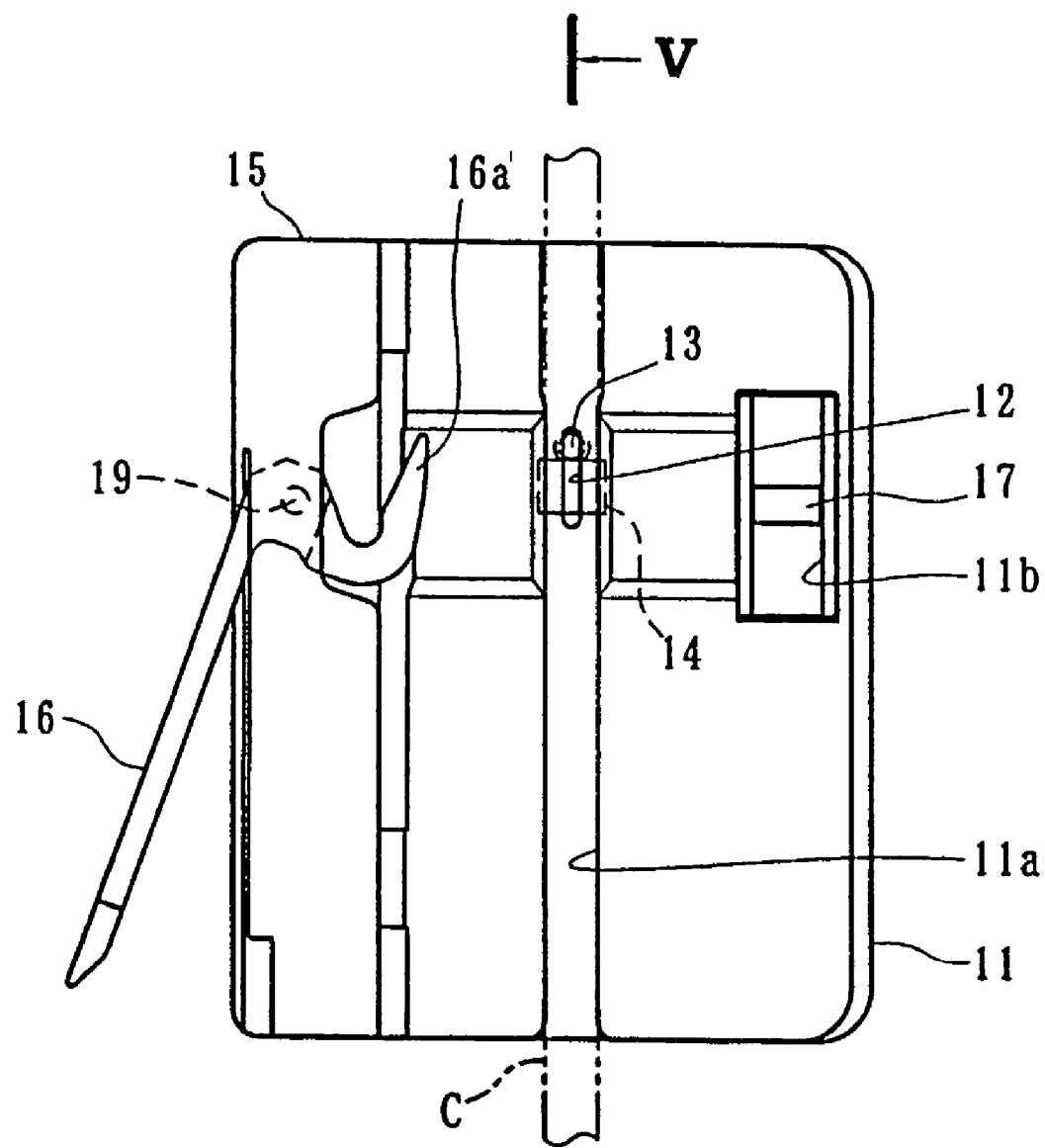
FIG. 4 is a top view of a hematocrit sensor with an opened cover in accordance with the present invention.
Figure 5:
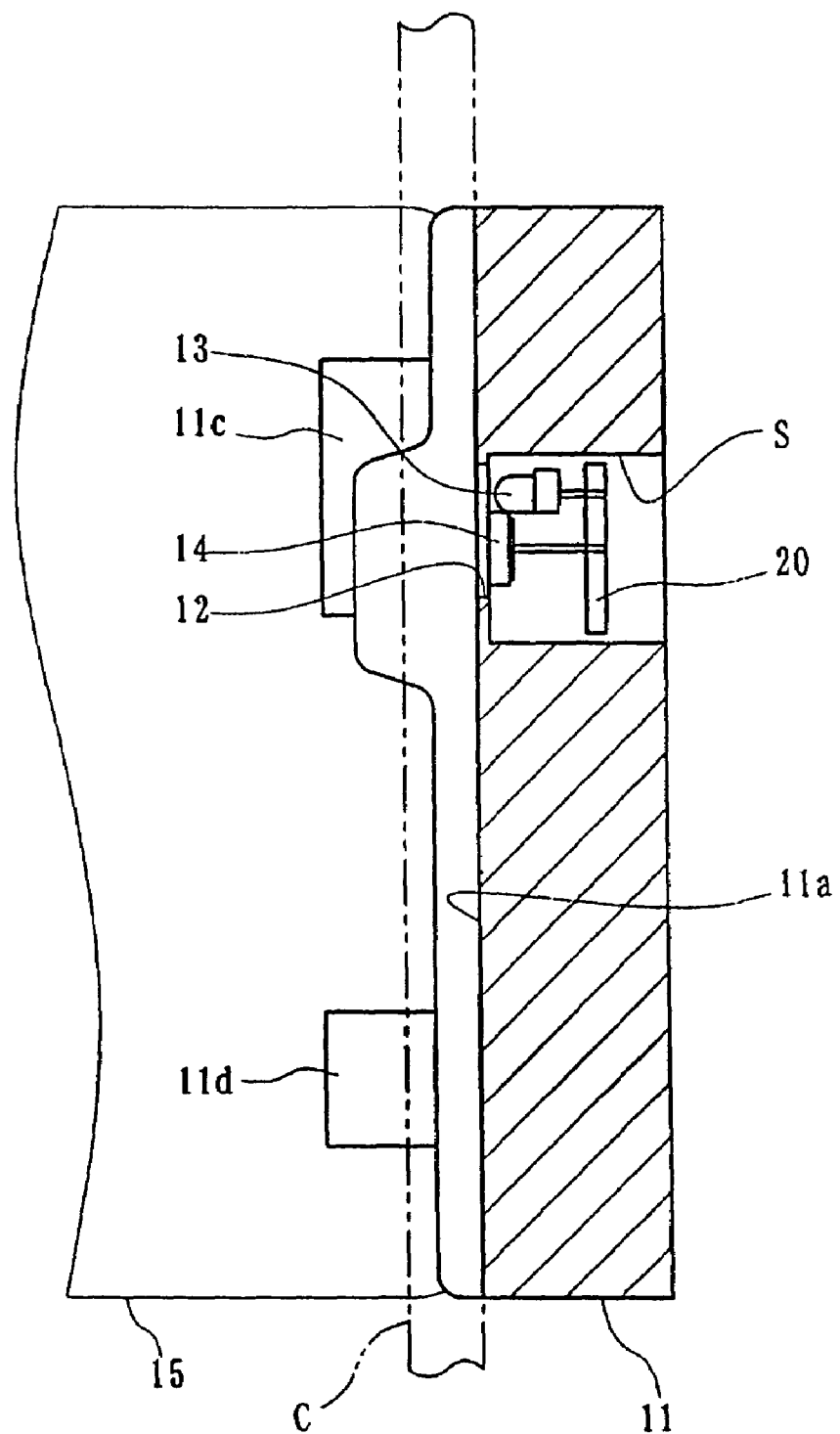
FIG. 5 is a cross sectional view at the V-V line in FIG. 4.

In addition, the surface of the housing 11 shown on the right side of FIG. 4 comprises a concave part 11b, inside of which pins 17 are fixed. Also, the surface of the housing shown on the left side of FIG. 5 comprises convex parts 11c and 11d to allow the cover 15 to swing freely.

The cover 15 can cover the front surface side of the housing 11 (the surface side having the slot 11a) and can also swing freely against the housing 11. Specifically, the swing pin 18 shown in FIG. 3a is inserted along the edge of the convex parts 11c and 11d and the cover 15, such that the cover 15 can rotate around the swing pin 18. Accordingly, the cover 15 can be opened or closed, allowing the slot 11a to be covered or uncovered.

Further, the edge of the cover 15 (the opposite edge of the edge having the swing pin 18) comprises a fixed pin 19 at the center of a freely movable hook 16. The hook 16 can hold the cover 15 against the housing 11 while the cover 15 is closed (i.e., covering the surface of the housing 11), such that the top part 16a, which has a key-like shape, is held by the pin 17. Further, the cover 15 is removable and can freely swing open against the housing, leaving the slot 11a covered when the cover 15 is closed and attached to the housing and uncovered when the cover 15 is swung open against the housing.

The slit 12 is formed by cutting a defined length along the bottom surface of the slot 11a in the direction of the extension of the slot 11a. Further inside the slit 12 of the housing 11 is a space S (see FIG. 5) that contains the light emission means 13 and light reception means 14, wherein the slit 12 fully connects the space S and the slot 11a. Instead of the slit 12, the plurality of pores formed at the bottom surface of the slot 11a may be employed, wherein the light irradiated from the light emission means and the reflected light can both pass through the plurality of pores to the light reception means. In addition, the slot 11a comprises a clear adhesive seal (not shown) to prevent water and other undesirable materials from entering the space S through the slot 11a.

Figure 6:
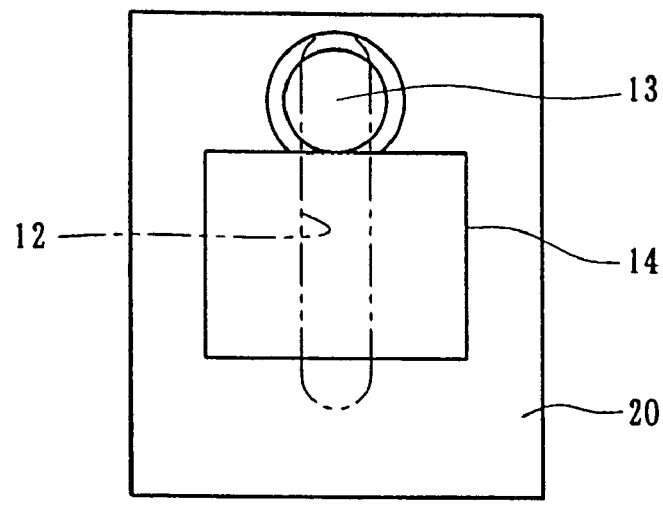
FIG. 6 is a schematic drawing of a hematocrit sensor comprising a light emission means (light emission element) and a light reception means (light reception element) in accordance with the present invention.

The light emission means 13 can comprise a light emitting diode (LED) (near infrared LED) that can irradiate a near infrared ray of approximately 805±15 nm wavelength. The light reception means 14 can comprise a photo diode. As shown in FIG. 6, the light emission means 13 and the light reception means 14 are located at a defined distance from each other on a base board 20, and are set in the space S. Both the light emission means 13 and the light reception means 14 can face the outside of the space S (specifically, the flexible tube C contained in the slot 11a) through the slit 12.

Further, the base board 20 functions as an amplification circuit to amplify the signal from the light reception means 14. The light reception means 14 receives the light and outputs a signal in accordance with the illumination. The signal can be amplified by using the amplification circuit. Further, according to this embodiment, when a near infrared LED is employed as the light emission means 13, it can irradiate the light at a wavelength that may not affect the light absorption ratio of hemoglobin. Thus, an accurate hematocrit value can be constantly measured without being effected by the oxygenation level of hemoglobin in the blood.

The light irradiated from the light emission means 13 passes to the flexible tube C, which is contained in the slot 11a, through the slit 12 and then reflects off of the blood flowing in the inside of the flexible tube C. The reflected light is then received by the light reception means 14 (a so-called reflection type sensor). Accordingly, in comparison with a so-called transmission type sensor, the reflection type sensor can prevent deformation of the flexible tube comprising the blood circuit and also allows the overall size of the sensor to be reduced.

The conventional light transmission type hematocrit sensor must strongly sandwich the flexible tube in order to increase the measuring accuracy using a light emission means and light reception means that face each other. In contrast, according to this embodiment of the present invention, the light reflection type hematocrit sensor comprises a flexible tube that is not strongly sandwiched by a light emission means and light reception means that face each other, and therefore this reflection type sensor does not bend and deform the flexible tube.

Furthermore, the light transmission type sensor must comprise one housing with an independent light emission means and another housing with an independent light reception means, thus increasing the total size of the sensor. In contrast, according to this embodiment of the present invention, the light reflection type sensor comprises only one housing having both a light emission means and a light reception means, thus allowing for the total size of the sensor to be reduced.

Additionally, the light transmission type sensor must comprise another part, a cuvette, in the measuring portion, such that the emitted and received light must pass through the cuvette. In contrast, according to this embodiment of the present invention, the light reflection type sensor does not require an extra part such as a cuvette, and thereby can reduce the number of parts and increase the operational productivity of the sensor.

A hematocrit value can be obtained based on an electric signal output from the light reception means 14. Specifically, each component of blood, such as red blood cells and blood plasma, has its own characteristic light absorption. By using this property, red blood cells which are required for measuring hematocrit value, can be electro-optically quantified, thus allowing the hematocrit value to be determined. When near infrared light irradiated from the light emission means reflects off of the blood, it is effected by absorption and scattering before it is received by the light reception means. Thus, a hematocrit value can be calculated by analyzing the light absorption and scattering ratio based on the strength of the received light.

By controlling the ultrafiltration pump 8 based on the measured hematocrit value (or various other calculated parameters, such as the rate of change of the circulating blood volume ($\Delta BV$)), a water removal rate, which is appropriate for the patient's condition, can be determined. Additionally, according to this embodiment of the present invention, the substitution fluid condition or dialyzing fluid condition may also be determined based on the measured hematocrit value.

Further, according to an embodiment of the present invention, the hematocrit sensor 7 has a fixed metal plate 21 on the outside of the housing 11. The plate 21 has a holder 22 formed by bending a metal plate. Such holder 22 has a fixed screw N, wherein the top of the screw N and the holder 22 are structured so as to hold a stand ST in order to fix the hematocrit sensor in place.

The mechanisms of the hematocrit sensor of the present invention are described below.

As previously shown in FIG. 1, the hematocrit sensor of the present invention is connected to the arterial blood circuit 1a. This connecting operation requires that the flexible tube C consisting of a part of the arterial blood circuit 1a is inserted along the slot 11a while the cover 15 is open (specifically, while the slot 11a is uncovered), and then the cover 15 is swung closed. Further, the hematocrit sensor 7 is fixed to the stand ST by fastening the fixed screw N.

The cover 15 can close the slot 11a, including the slit 12, by closing the cover 15. Accordingly, the cover 15 and the housing 11 can sandwich the flexible tube C (FIG. 3a). In this case the preferred sandwiching force is in a range that will not deform the flexible tube C. For this purpose, the width and depth of the slot 11a are preferably designed to be approximately the same as the outer diameter of the flexible tube C.

Accordingly, the slot 11a, including the slit 12, is closed with the cover 15, such that the effect of the ambient light can be controlled, and emission and reception of the light between the light emission means 13 and the light reception means 14 are accurate. Thus, a more accurate hematocrit value can be measured. Furthermore, it is acceptable to use another cover that can cover the slot 11a, including the slit 12, other than the cover of this embodiment if the cover can entirely cover the slot 11a of the housing 11. Alternatively, a cover that only covers the upper part of the slot 11a may be also employed.

After the cover 15 is closed, the hook 16 is swung to hold the cover 15 against the housing 11. Accordingly, after the hematocrit sensor is connected to the blood circuit 1, the sensor can be prevented from slipping out of position or the cover 15 can be prevented from being carelessly opened. Thus, a more accurate measurement of the hematocrit value can be obtained.

Further, the cover 15 can swing freely against the housing 11, such that the slot 11a, including the slit 12, can be opened and closed. The cover 15 can be swung closed after the hematocrit sensor is connected to the blood circuit 1 and during measurement of the hematocrit value. Also, the cover 15 can be swung open and the flexible tube C can be removed when the hematocrit value is not being measured or when the hematocrit sensor is disconnected from the blood circuit. Thus, operational productivity can be increased by connecting the sensor to the blood circuit and disconnecting it from the blood circuit.

As mentioned above, the hematocrit sensor is connected to the arterial blood circuit 1a. Dialysis treatment is then performed, wherein the hematocrit sensor 7 can perform real-time measurements of the hematocrit value. Specifically, the light (near infrared ray) from the light emission means 13 is irradiated to the blood flowing through the flexible tube C in the slot 11a. The light reception means 14 receives the reflected light. The light reception means 14 then outputs an electric signal of voltage in accordance with the illumination of the received light. The hematocrit value can be determined based on this output signal.

As mentioned above, according to this embodiment, an extra part, such as a cuvette for a transmission type sensor, is not required. The measurement can be performed simply using the flexible tube. Therefore, the number of parts can be reduced and costs can be lowered. Of course, the measurement accuracy can be increased by using specialty parts, such as a cuvette.

Figure 7:
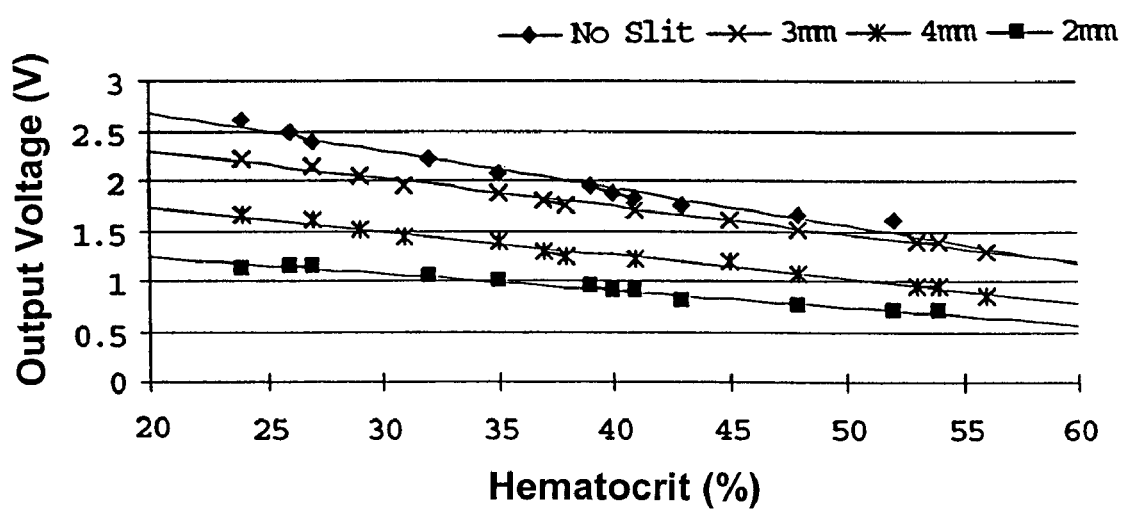
FIG. 7 is a graph showing the output voltage from a light reception means in a hematocrit sensor at no-slit, 2 mm slit width, 3 mm slit width, and 4 mm slit width.

A graph showing the relationship between hematocrit value and output voltage is shown in FIG. 7. This graph shows each relationship between hematocrit values (%) measured from a hematocrit sensor having varying slit widths: no slit, 2 mm, 3 mm, and 4 mm, and the corresponding output voltage from the light reception means 14. As shown in the graph, when a particular slit width is employed, in a practical hematocrit value range of 20 to 60%, the output voltage is proportional. Thus, a more accurate measurement can be obtained, and compensation is not required. Depending on the individual patient, the hematocrit value may vary in the range of 10 to 60%, but the aforementioned slit width the relationship will still be proportional.

A slit width is in the range of 2 to 4 mm is preferable because a more linear output voltage can be obtained in the practical range of the hematocrit value. A slit width of 3 mm is most preferable. Furthermore, although a slit width of 2 to 4 mm is preferred, other slid widths can be employed depending on the diameter of the flexible tube. Additionally, when a plurality of pores is employed instead of a slit, a pore diameter of 2 to 4 mm is preferred.

During dialysis treatment, the blood pump is driven to pump the patient's blood and circulate it extracorporeally. The blood is collected through the arterial needle a and flows through the arterial blood circuit 1a to the dialyzer 2. From there, the blood flows through the venous blood circuit 1b and returns to the patient through the venous needle b. During this process, materials such as contaminants are eliminated from the blood by the dialyzer 2. Additionally, water also can be removed from the blood.

Such water removal, as described earlier, is performed by driving the ultrafiltration pump 8. A certain amount of water is forcefully removed from the blood that flows through the blood circuit of the dialyzer 2 (i.e., through the inside of the hollow fiber). The water removal rate is controlled based on the hematocrit value measured by the hematocrit sensor. More specifically, the control is based on the rate of change of the circulating blood volume. The rate of change of the circulating blood volume (ΔBV) can be determined using the following formula:

$$\Delta BV = \frac{(Ht \text{ at the start of dialysis} - Ht \text{ at the time of measurement})}{Ht \text{ at the time of measurement}} \times 100$$

The hematocrit sensor 7 measures the hematocrit value in real-time, which indicates the patient's blood concentration. Feedback based on the measured value is sent to the driving control means for the ultrafiltration pump 8. Thus, water can be removed at an appropriate rate based on the patient's condition. If the measured value is normal, water is removed at the pre-set rate. But if the hematocrit value rises above normal, the increased blood concentration may cause the patient to suffer shock or a drop in blood pressure. In that case, the water removal rate would be decreased by controlling the driving of the ultrafiltration pump 8.

According to this embodiment, although the hematocrit sensor 7 is in the arterial blood circuit 1a, it can be positioned in the venous blood circuit 1b. In this situation, the arterial hematocrit value (Hta) must be calculated from the venous hematocrit value (Htv) using, for example, the following formulas:

Specifically, the following formula represents the relationship between the arterial and venous hematocrit values:

$$Htv = \frac{Qb}{(Qb - Qu)} \times Hta$$

Therefore, the following formula can be obtained:

$$Hta = \frac{(Qb - Qu)}{Qb} \times Htv$$

The blood flow rate (Qb) and water removal rate (Qu) through the arterial blood circuit 1a are known. Therefore, Htv can be measured and Hta can be calculated.

Figure 8A:
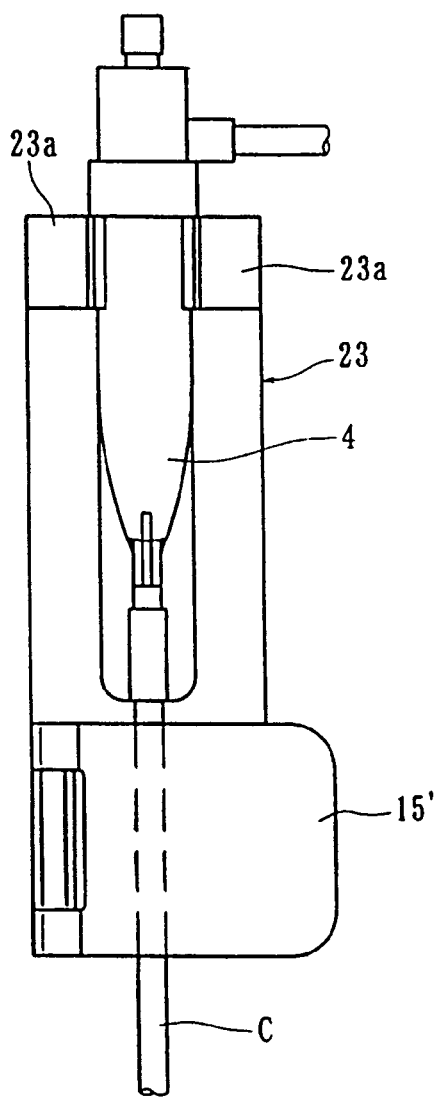
FIG. 8a is a front view of a hematocrit sensor integrally formed with a fixing means for a drip chamber in accordance with the present invention.
Figure 8B:
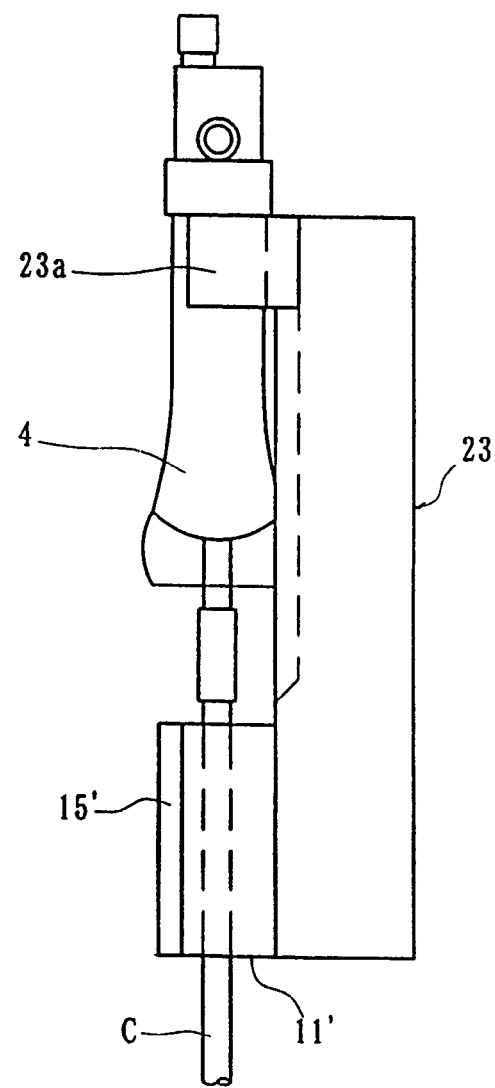
FIG. 8b is a right side view of a hematocrit sensor integrally formed with a fixing means for a drip chamber in accordance with the present invention.

According to another embodiment shown in FIG. 8, the hematocrit sensor comprises a housing 11 and a fixing means 23 (i.e., a stand for a drip chamber 4) are integrally formed, and a drip chamber 4 is connected to the blood circuit 1. The housing 11 is formed as a lobe at one end of the integrally formed fixing means 23 and drip chamber 4.

FIG. 8 also shows a pair of lobes 23a that hold the drip chamber 4, wherein the slot formed in the housing 11' connects a part of the extended flexible tube C from the lower end of the drip chamber 4. The cover 15' can close the slot when the cover 15' is closed and is able to freely swing against the housing 11'.

The same slit as in previous embodiments is formed in the slot of the housing 11'. Light emission and light reception, which occurs between the light emission means and the light reception means, is performed through the slit. Accordingly, the hematocrit value of the blood flowing through the flexible tube C can be measured. Based on the measured hematocrit value, the ultrafiltration pump can be controlled. The slot, light emission means, and light reception means are not shown in the figure because they are similar to those shown and described in previous figures described above.

Furthermore, although the cover 15' has no means for being held against the housing 11' as in a previous embodiment, the hook 16 can be built and added to the assembly as a means for holding. According to this embodiment, although the hematocrit sensor is integrally formed with the fixing means 23 for the drip chamber 4, which is connected to the venous blood circuit 1b, the drip chamber can alternatively be connected to the arterial blood circuit 1a. Even in this situation, the hematocrit sensor can still be integrally formed with the fixing means 23 for the drip chamber 4.

In addition to the hematocrit sensor being integrally formed with the fixing means for the drip chamber, the hematocrit sensor housing and the air bubble detector connected to the venous blood circuit 1b can also be commonly integrally formed. Of course, the hematocrit sensor and other structuring means connected to the blood circuit 1 can be integrally formed as well.

As described above, the hematocrit sensor can be integrally formed with the fixing means for the drip chamber or the air bubble detector. Accordingly, the blood circuit and surrounding components can be simplified and reduced in size in comparison with hematocrit sensors having parts that are separate and not commonly integrally formed. By unifying various components, both the integrally formed components and the hematocrit sensor can be set in place at the same time, allowing for a complicated arrangement step to be simplified.

Figure 9:
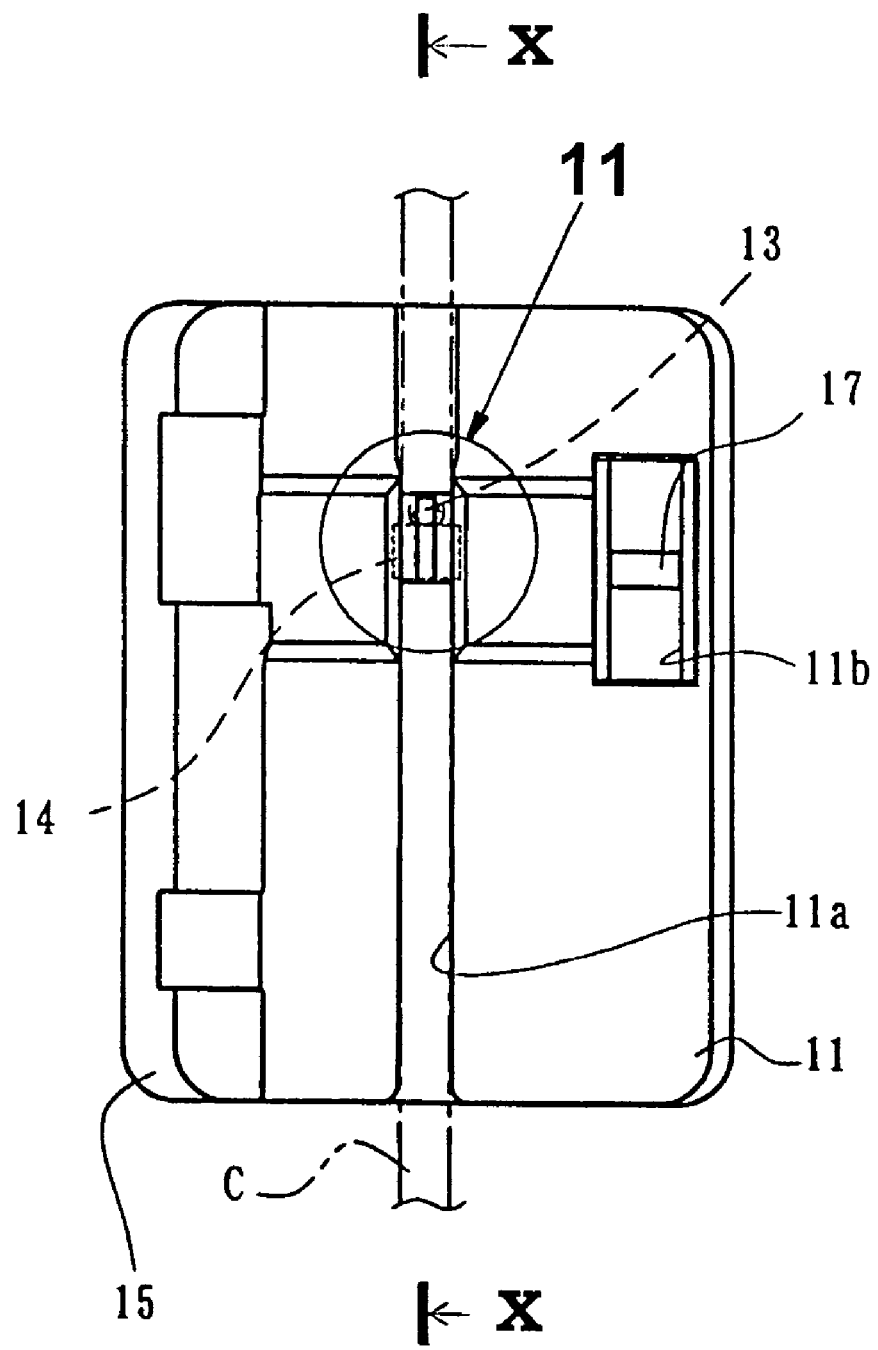
FIG. 9 is a top view of a hematocrit sensor with an opened cover in accordance with the present invention.
Figure 10:
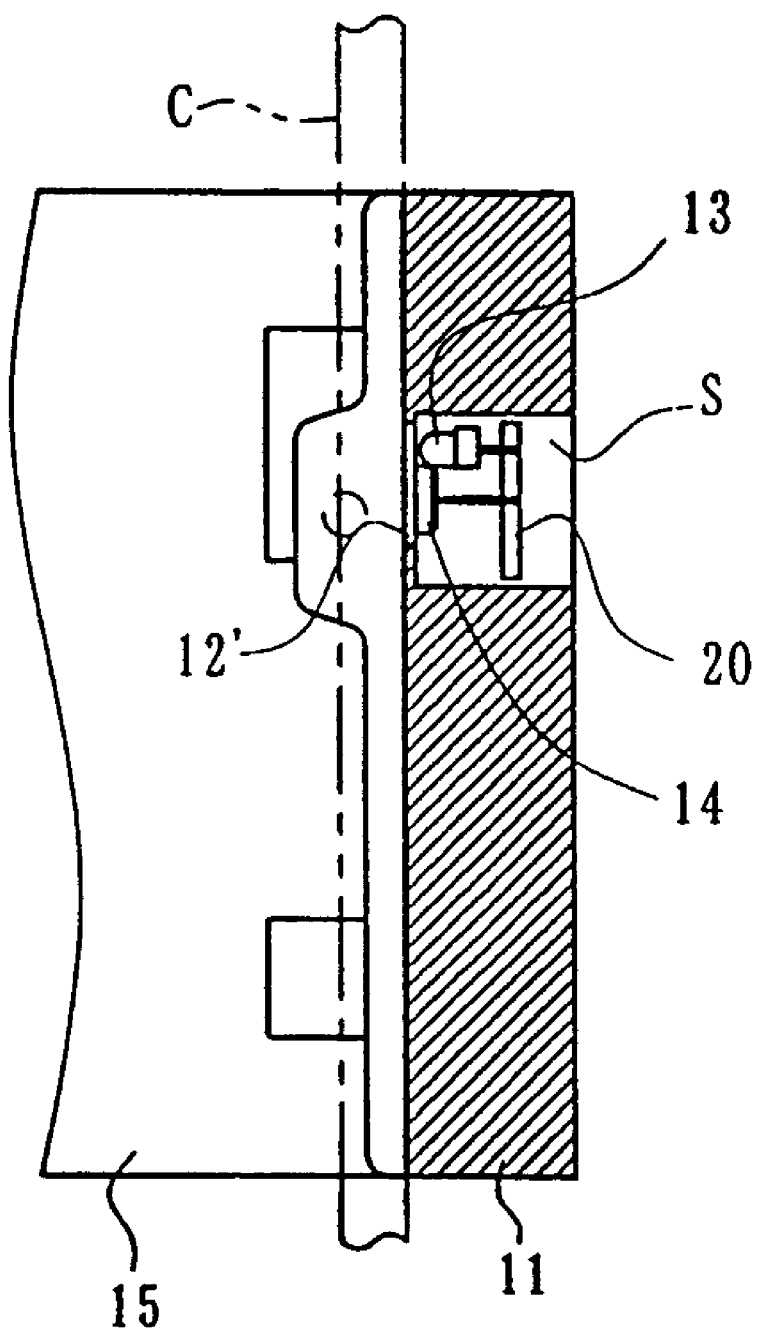
FIG. 10 is a cross sectional view at the X-X line in FIG. 9.

According to another embodiment shown in FIGS. 9 and 10, the hematocrit sensor comprises a housing 11, a slit 12', a base board 20 comprising a light emission means 13 (a light emitting element) and a light reception means 14 (a light receiving element), and a cover 15. Further, the housing comprises a slot 11a, as described above in connection with previous embodiments, and a space S that can contain the base board 20. The components shown in FIGS. 9 and 10, which appear in previous figures, have been assigned the same reference numerals as in those previous figures. Accordingly, a detailed description of these components is not given. Additionally, the hook used to hold the cover 15 against the housing 11 is not shown.

Figure 11:
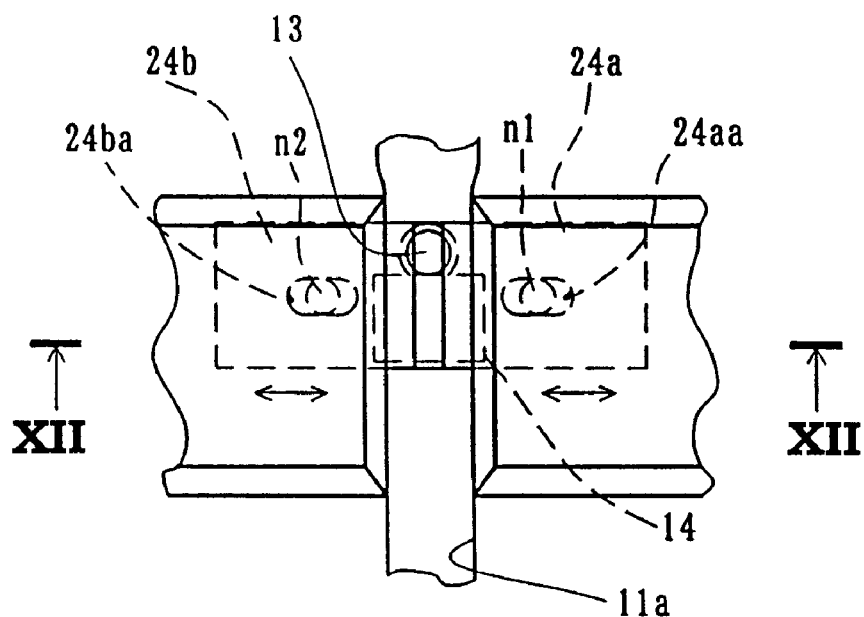
FIG. 11 is an enlarged view of portion A in FIG. 9.
Figure 12:
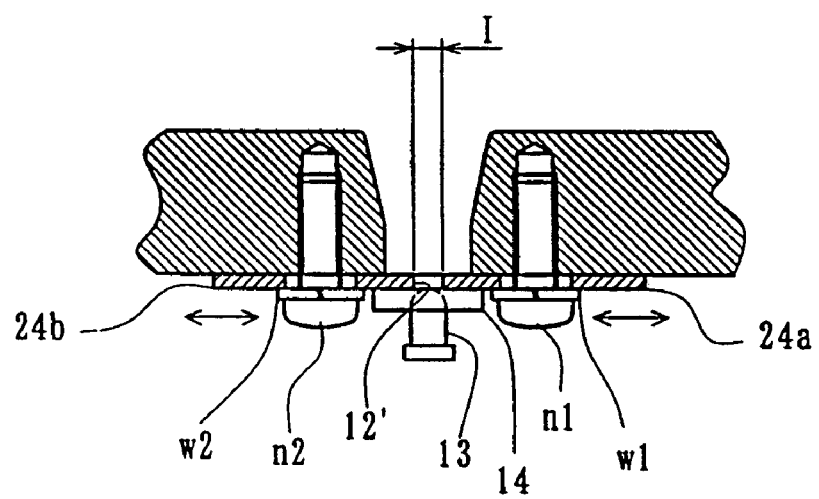
FIG. 12 is a cross sectional view at the XII-XII line in FIG. 11.

According to this embodiment, the hematocrit sensor comprises the slit 12' having an adjustable width. Specifically, as shown in FIGS. 11 and 12, the slit 12' comprises a gap between two boards 24a and 24b. The gap width can be made narrower by bringing boards 24a and 24b closer together, and wider by keeping boards 24a and 24b further apart from each other.

Boards 24a and 24b comprise long holes 24aa and 24ba respectively. Screws n1 and n2 can be connected to long holes 24aa and 24ba through washers W1 and W2, respectively. Thus, the width between boards 24a and 24b can be freely adjusted and fixed. Specifically, boards 24a and 24b can be slid within the length of the long holes 24aa and

24ba, and can also be fixed at any desired position within that length using screws n1 and n2.

Accordingly, the slit width can be easily adjusted to give a proportional relationship between the hematocrit value (%) and the output voltage of the light reception means 14. Thus, an accurate hematocrit value measurement can be obtained. The flexible tube C comprising the blood circuit 1 can have one of various inside diameters due to different wall thicknesses even though the flexible tube C maintains the same outside diameter. Also, the flexible tube C can have one of various different reflections of light from the light emission means 13 due to the different surface (due to an embossing process, for example). These variations can be taken into consideration and the slit width can be adjusted based on the effect of the output voltage of the light reception means due to the aforementioned variations. Thus, errors due to such variations can be avoided.

The width and the depth of the slot 11a, which holds the flexible tube C, can vary as well in response to different types of flexible tube C having different outside diameters. Further, the slit width of the upper part of the light emission means 13 and the slit width of the upper part of the light reception means 14 can be made independently adjustable. The medial axis of the slit 12' and the medial axis of the flexible tube C held by the slot 11a do not always have to be positioned along the same straight line. Rather, they can be made adjustable due to the direction of the light emission means 13 fixed on the board 20. Furthermore, if the plurality of pores is employed instead of the slit 12', each pore can be made adjustable using a variable diaphragm. In this case, the position of the pores in addition to the diameter of the pores could be adjustable, thus allowing for fine adjustment.

Figure 13:
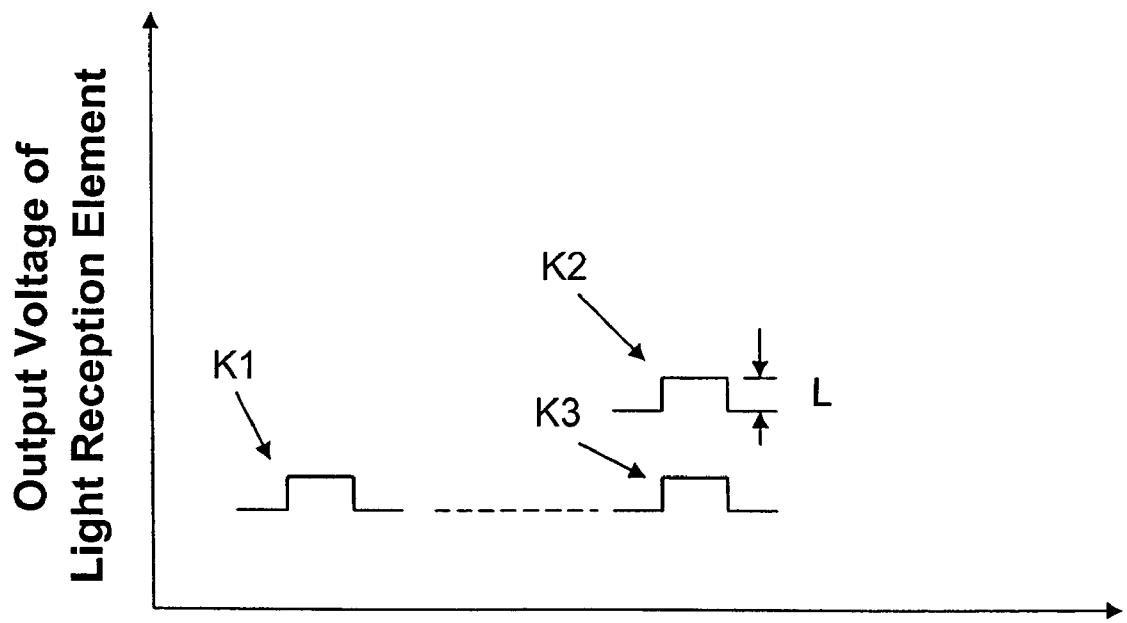
FIG. 13 is a graph showing the output voltage waveform from the light reception means in a hematocrit sensor of the present invention.

According another embodiment of the present invention, the hematocrit sensor comprises a flashing means that turns the light emission means on and off. The hematocrit sensor monitors the output voltage from the light reception means when the light emission means is turned off. For example, as shown in FIG. 13, the output voltage of the light emission means can be monitored when the light emission means is turned off by determining the output voltage waveform (K1) of the light reception means when there is no ambient light.

If the output voltage waveform of the light reception means changed to a different output voltage waveform (K2) due to the irradiation of ambient light to the light reception means when the light emission means is turned off, output voltage waveform K2 can be regenerated, as if it is output voltage waveform K1, while the light emission means is turned off. The regenerated output voltage waveform (K3) is a detectable waveform. The regeneration can be performed on each flashing of the light emission means, and the regenerated output voltage can be compensated each time. Furthermore, instead of the regeneration of the output voltage waveform K3 from the output voltage waveform K2 based on the output voltage waveform K1, the difference between the on-state and off-state of the light emission means can be used to determine the output voltage. The composition of the hematocrit sensor itself can be as the same as one of the previous embodiments, or it can be different, wherein controlling the light emission means and monitoring the light reception means is performed as described above.

As discussed earlier, measurement errors due to ambient light can be avoided, measurement accuracy can be increased, and safety of the medical equipment can be increased. A seal for protecting the slit from irradiation of ambient light can be simplified or removed, thereby simplifying the composition of the hematocrit sensor itself.

Figure 14:
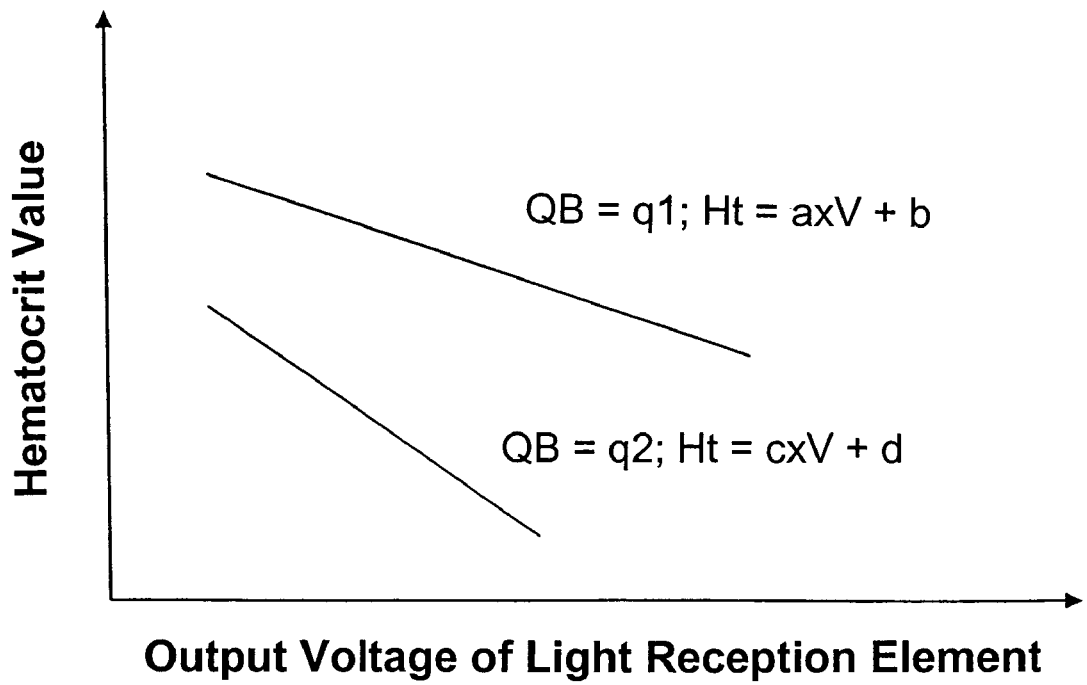
FIG. 14 is a graph showing the relationship between the hematocrit value and the output voltage from a light reception means when the hematocrit value depends on the blood flow rate.

According to another embodiment, the hematocrit sensor measures the hematocrit value based on differences in blood flow rates through the flexible tube C. In some cases, the relationship between an output voltage of the light reception means and a hematocrit value depends on the blood flow rate (QB). For example, as shown in FIG. 14, when QB equals q1 or q2, the relationship between the output voltage and the hematocrit value is expressed differently when QB equals q1 versus when QB equals q2.

Therefore, according to this embodiment, the relationship between the output voltage of the light reception means and the hematocrit value when QB equals q1 (expressed as Ht=a×V+b where a and b are constants) can be stored in the sensor. While the initial QB equals q1, the hematocrit value is continuously measured. When QB equals q2, the hematocrit value can be continuously measured as if QB equals q1 by automatically controlling the blood pump in the blood circuit.

After the measurement of the hematocrit value, the blood pump is automatically controlled to change QB from q1 to q2. When the hematocrit value is the same at both q1 and q2, the calculation of the hematocrit value deviates depending on the blood flow rate. Accordingly, after changing the flow rate to q2, the hematocrit value can be recalculated with compensation as if QB equals q1, and hematocrit values can be continuously measured. After recalculation, a variation ($\Delta$Ht/$\Delta$V) of the hematocrit value per voltage unit employs the same constant value a as when QB equals q1.

Figure 15:
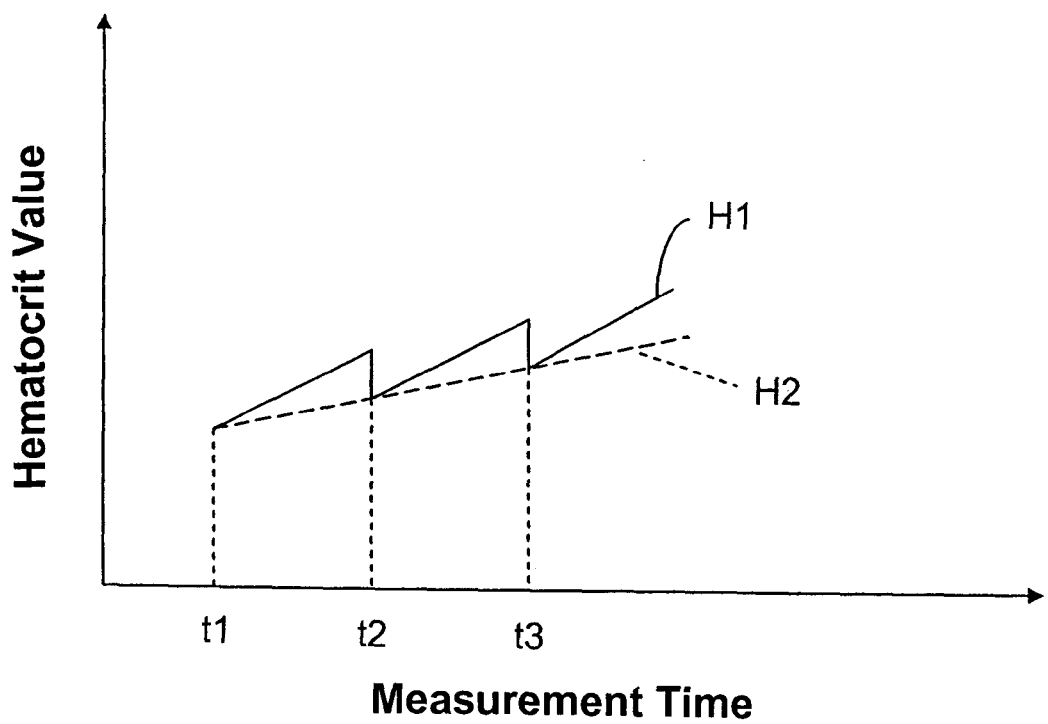
FIG. 15 is a graph showing the measured value of H1 using the constant a from the equation where QB equals q1, wherein QB is the blood flow rate through the hematocrit sensor, and H2 is the actual variation in the hematocrit value in accordance with the present invention.

When QB equals q2, however, the relationship between the output voltage of the light reception means and the hematocrit value is expressed as Ht=c×V+d, where c and d are constants. Because of the difference between constant value c (when QB equals q2) and constant value a (when QB equals q1), there can errors in the measured hematocrit values. Therefore, QB can be automatically converted to q1, in which the relational expression is known, and the hematocrit value can be measured. Then, when QB is automatically changed to q2, the hematocrit value can be compensated to be the same value as when QB equaled q1, and the hematocrit measurement can be continuously performed. The compensation can be performed at a time when the variation of the hematocrit value exceeds a certain range, or when the measuring duration exceeds a certain length of time. For example, as shown in FIG. 15, when compensations are performed at measurement times t1, t2, and t3, the variation of the actual hematocrit value is H2. When QB employs constant value a (when QB equals q1), the compensated measurement value changes as H1.

Figure 16:
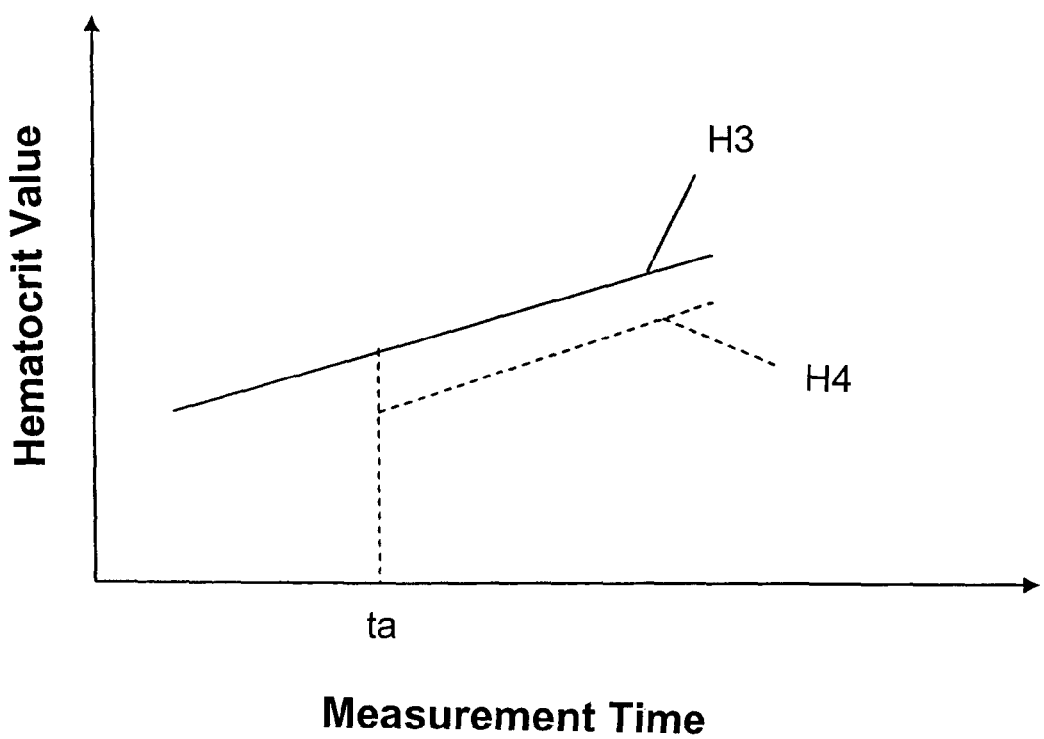
FIG. 16 is a graph showing the change H4 of the after-changed hematocrit value when the blood flow rate (QB) is changed from q2 to q3 at time ta during ongoing measurement by the hematocrit sensor, and the change H3 of the before-changed hematocrit value in accordance with the present invention.

Further, as shown in FIG. 16, when QB changes from q2 to q3 at time ta during continuous measurement, the hematocrit value just after QB changes (H4 in FIG. 16) is compensated to become the hematocrit value just before QB changed (H3 in FIG. 16), and the hematocrit measurements are continuously obtained. As shown in FIG. 15, the compensation of the hematocrit value is repeatedly performed. Further, if the hematocrit sensor is independent from a blood purifier, the sensor can be electrically connected to the blood purifier in order to continuously collect blood flow rate information.

According to this embodiment, based on the blood flow rate of the blood flowing through the flexible tube C, the detected hematocrit value can be compensated, thereby avoiding measurement errors due to a difference in blood flow rates. Consequently, more accurate hematocrit value measurements can be obtained.

Figure 17:
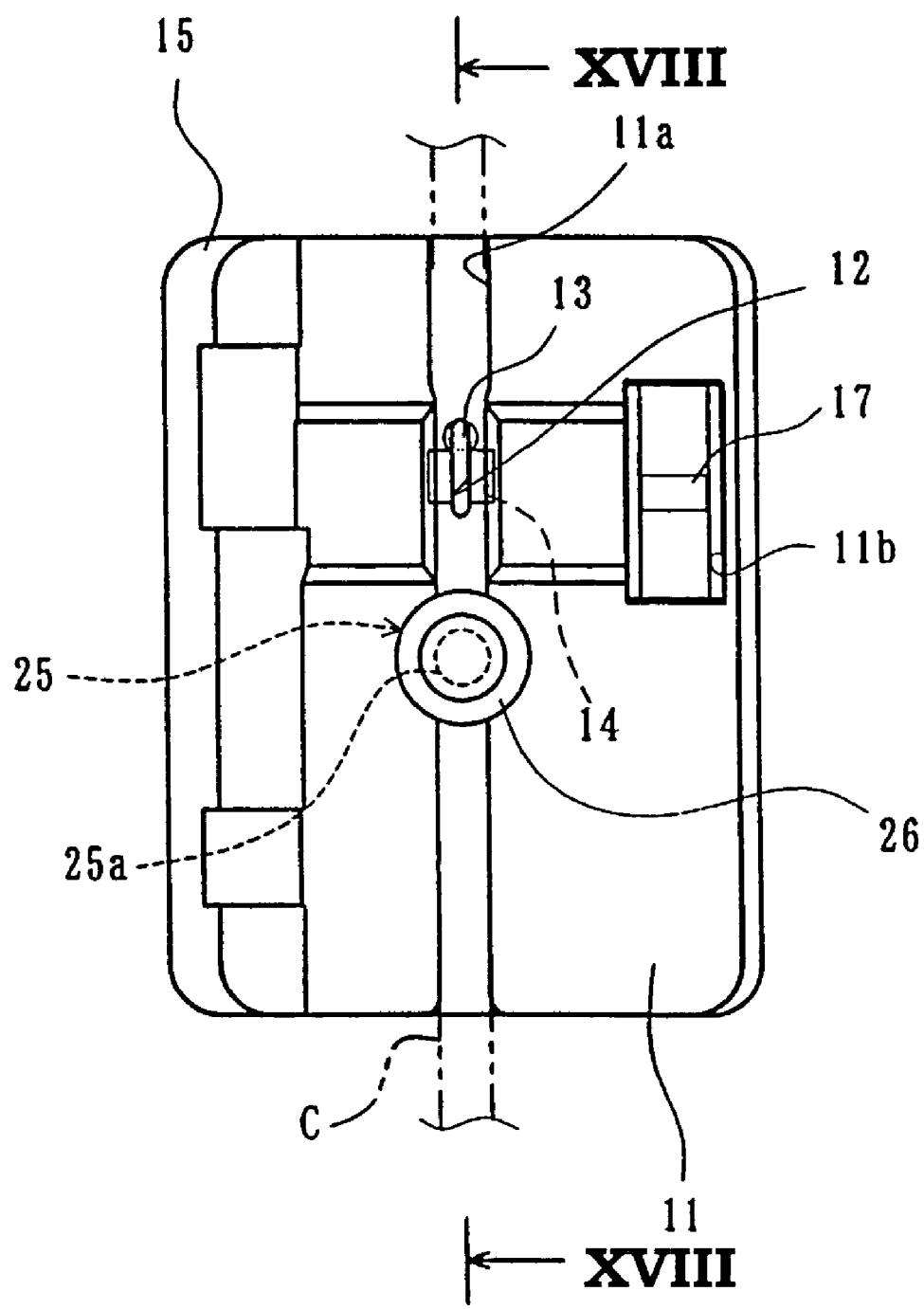
FIG. 17 is a top view of a hematocrit sensor with an opened cover in accordance with the present invention.
Figure 18:
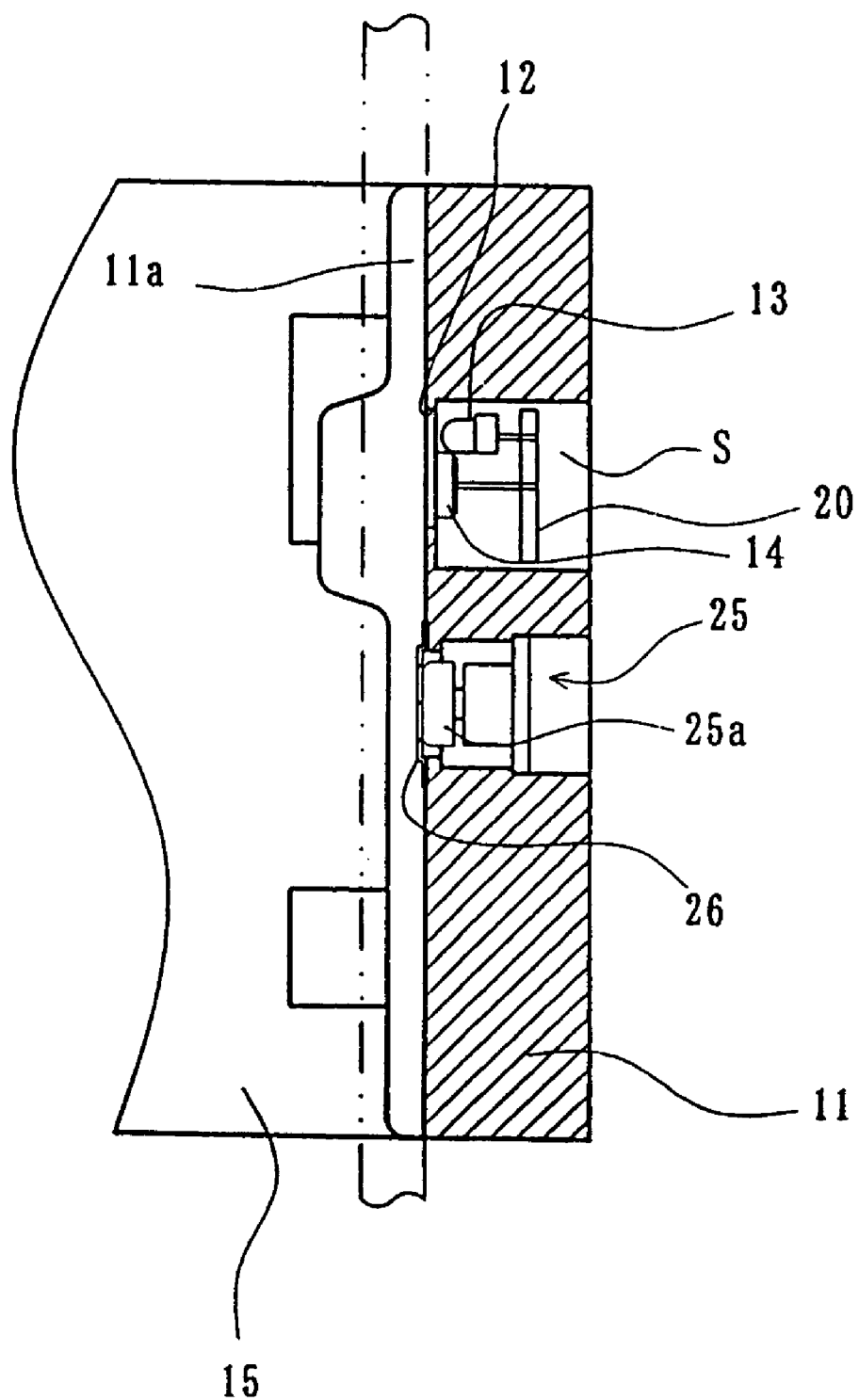
FIG. 18 is a cross sectional view at the XVIII-XVIII line in FIG. 17.

According to another embodiment of the present invention, as shown in FIGS. 17 and 18, the hematocrit sensor comprises a housing 11 having a slot 11a with a slit 12, a base board 20 comprising a light emission means 13 and a light reception means 14, a cover 15, and a detection switch 25 as a means for detecting whether the cover is open or closed. The components shown in FIGS. 17 and 18, which appear in previous figures, have been assigned the same reference numerals as in those previous figures. Accordingly, a detailed description of these components is not given. Additionally, the hook used to hold the cover 15 against the housing 11 is not shown.

The switch 25 detects whether or not the flexible tube C in the blood circuit is contained in the slot 11a, and whether or not the cover 15 is closed. The switch 25 comprises a push button portion 25a positioned slightly above the bottom of the slot 11a. After the flexible tube C is placed into the slot 11a and the cover 15 is closed; the push button portion 25a is pressed through the flexible tube C, and turns on the detection switch. Furthermore, the flexible cover 26 seals the detection switch 25, preventing water or undesirable materials from entering through the slot 11a.

When the detection switch is turned on, it can recognize that the cover 15 is closed after the flexible tube C is set in place. Accordingly, instances of forgetting to set the flexible tube C in the slot 11a of the hematocrit sensor and then closing the cover 15 can be avoided. Also, measuring errors due to irradiation of ambient light can be avoided as well.

In place of the aforementioned detection switch 25, other means can be employed that can detect whether or not the flexible tube C in the blood circuit is set in the slot 11a, and whether or not the cover 15 is closed. Further, when the hematocrit sensor is connected to a blood purifier and the hematocrit value is being measured, the blood purifier can be used to visually or audibly notify the operators when they forget to set the flexible tube C and to close the cover 15.

According to a further embodiment, the hematocrit sensor (including both type where components are integrally formed and the type where components are separate) can be co-driven with a blood detector (not shown) that is connected to the blood circuit 1. The blood detector can be built in the housing of air bubble detector 5, and analyzes the presence of blood in the blood circuit 1. Accordingly, the starting point for the hematocrit measurement can be adjusted as necessary.

When the ultrafiltration pump is controlled based on the rate of change of the circulating blood volume ($\Delta BV$), this variation is a relative value. Accordingly, if the starting point for hematocrit measurement is varied, every measurement cannot be compared. In contrast, if the starting point is adjusted after a certain period of time (e.g., at the time when flow begins), every measurement can be accurately compared.

If the hematocrit sensor is integrally formed with a blood detector, the effect of recirculation in the shunt part of the blood circuit when saline solution is directed to the patient's body (i.e., when the blood diluted with saline is incorporated into the blood circuit, the hematocrit value decreases) can be eliminated.

Further, the blood detector conventionally is connected to the venous blood circuit 1b, and it is desirable for the blood detector and the hematocrit sensor to be integrally formed. However, even when the blood detector is connected to the arterial blood circuit 1a, the blood detector and the hematocrit sensor can still be integrally formed, for example, where the blood detector is built in the housing.

Although various embodiments of the present invention have been described, the present invention is not limited to these embodiments. For example, other types of dialysis devices and blood circuits can be used. Specifically, the dialysis device used in these embodiments is a so-called central system, which separately comprises a dialyzing fluid supplier and a dialysis monitor, but an integrally formed system (a so-called personal dialysis apparatus) can be used instead.

Further, according to the present embodiments, the duplex pump P in the dialysis monitor supplies dialyzing fluid to the dialyzer 2, but a so-called balancing chamber can also be employed to supply dialyzing fluid. Also, a double needle type comprising an arterial needle and a venous needle is described in the present embodiments, but a single needle type which having only one needle can also be used.

The hematocrit sensor of the present invention is not limited to uses in connection with dialysis treatment, and can also be applied to various blood purifiers which extracorporeally circulate the blood. Additionally, the blood circuit is not limited to the flexible tube. Rather, various circuits through which blood is able to flow an be employed as a blood circuit.

Further, a hematocrit sensor comprising the flexible tube C in the blood circuit 1, which is contained in the slot 11a built in the housing 11, can be used without the component cover 15. In this case, the light emitting from the light emission means and the light reception at the light reception means can be performed through the slit 12. Of course, a means to fix the stand ST (e.g., holder 22 and screw N) is not required and other fixing means can be employed. The light emission means and the light reception means are not limited to a LED and photodiode in accordance with the present embodiments and other light emission and light reception means which can measure the reflected light of irradiated light and the hematocrit value can be employed.

We claim:

1. A hematocrit sensor comprising:
 a blood circuit having two ends;
 a blood purifier connected to said blood circuit between said two ends and configured to purify blood that is being circulated extracorporeally in said blood circuit; and
 a sensor connected to said blood circuit and configured to measure hematocrit values, the sensor including
  a housing connected to a portion of said blood circuit,
  a slot provided with said housing,
  a slit included in said slot of said housing, and
  a light emission device and a single light reception device provided adjacent to each other in said slot such that both said light emission device and said single light reception device are in optical connection with each other and positioned to face said blood circuit through said slit.

2. The hematocrit sensor of claim 1, further comprising a cover provided at said housing, which covers said slot when said cover is closed.

3. The hematocrit sensor of claim 1, further comprising a cover provided at said housing, which swings open against said housing and uncovers said slot when said cover is opened.

4. The hematocrit sensor of claim 2, further comprising a holding device configured to hold the cover in place when the slot is covered.

5. The hematocrit sensor of claim 2, further comprising a detection device configured to detect at least one of whether said blood circuit is in said slot, and whether said cover is closed.

6. The hematocrit sensor of claim 1, wherein said blood purifier configured to perform dialysis treatment.

7. The hematocrit sensor of claim 6, further comprising an ultrafiltration pump, a substitution fluid, and a dialyzing fluid.

8. The hematocrit sensor of claim 1, further comprising a drip chamber connected to said blood circuit.

9. The hematocrit sensor of claim 8, wherein said hematocrit sensor is provided with a fixing device at said housing of said sensor to fix said drip chamber.

10. The hematocrit sensor of claim 1, further comprising an air bubble detector provided with said housing of said sensor and connected to said blood circuit.

11. The hematocrit sensor of claim 1, further comprising a blood detector connected to said blood circuit and configured to detect a presence of blood in said blood circuit.

12. The hematocrit sensor of claim 1, wherein said slit has an adjustable width.

13. The hematocrit sensor of claim 1, wherein at least one of said plurality of pores has an adjustable diameter.

14. A method of measuring hematocrit values, comprising:
providing a sensor connected to a blood circuit, said sensor having a slot with a slit included in said slot,
providing a light emission device and a single light reception device adjacent to each other in said slot such that both said light emission device and said single light reception device are in optical connection with each other and positioned to face said blood circuit through said slit:
emitting light from said light emission device toward blood flowing through said blood circuit;
receiving said light at said single light reception device, said received light being emitted from said light emission device and reflected from said blood flowing through said blood circuit;
determining a light absorption received by said single light reception device; and
calculating hematocrit values based on a strength of said light absorption determined by said determining.

15. The method of claim 14, wherein:
said light emission device emits light intermittently; and
said hematocrit values calculated in said calculating are corrected based on a strength of an ambient light received by said single light reception device when said light emission device does not emit said light.

16. The method of claim 14, wherein said hematocrit values calculated in said calculating are corrected to compensate an error based on a flow rate of said blood flowing through said blood circuit.

17. The method of claim 15, wherein said hematocrit values calculated in said calculating are corrected to compensate an error based on a flow rate of said blood flowing through said blood circuit.

18. The method of claim 14, further comprising:
detecting a presence of said blood flowing through said blood circuit, wherein the calculating starts calculating a first of said hematocrit values at a time said detecting first detects said presence of said blood.

19. A hematocrit sensor comprising:
a blood circuit having two ends;
a blood purifier connected to the blood circuit between the two ends and configured to purify blood that is being circulated extracorporeally in the blood circuit; and
a sensor connected to the blood circuit and configured to measure hematocrit values, the sensor including
a housing connected to a portion of the blood circuit,
a slot provided with the housing,
a slit in the slot of the housing, and
a single light emission device and a single light reception device both provided adjacent to each other in said slot and configured to be in optical connection with each other and positioned to face the blood circuit through the slit.

* * * * *